(12) United States Patent
Igarashi (10) Patent No.: US 10,582,839 B2
(45) Date of Patent: Mar. 10, 2020

(54) IMAGE PICKUP UNIT, WIRING BOARD WITH CABLE, AND MANUFACTURING METHOD OF WIRING BOARD WITH CABLE

(71) Applicant: OLYMPUS CORPORATION, Tokyo (JP)

(72) Inventor: Takatoshi Igarashi, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 574 days.

(21) Appl. No.: 15/374,459

(22) Filed: Dec. 9, 2016

(65) Prior Publication Data

US 2017/0086660 A1    Mar. 30, 2017

Related U.S. Application Data

(63) Continuation of application No. PCT/JP2015/063307, filed on May 8, 2015.

(30) Foreign Application Priority Data

Jun. 16, 2014    (JP) .................................. 2014-123679

(51) Int. Cl.
*A61B 1/05* (2006.01)
*H05K 3/36* (2006.01)
(Continued)

(52) U.S. Cl.
CPC ............ *A61B 1/051* (2013.01); *A61B 1/0011* (2013.01); *G02B 23/2484* (2013.01);
(Continued)

(58) Field of Classification Search
CPC ... A61B 1/051; A61B 1/0011; G02B 23/2484; H04N 5/2253; H04N 2005/2255;
(Continued)

(56) References Cited

U.S. PATENT DOCUMENTS 4,831,456 A  *  5/1989  Takamura ................. A61B 1/05
                                                          348/294
2004/0132491 A1*  7/2004  Kim ..................... H04M 1/0218
                                                           455/556.1
(Continued)

FOREIGN PATENT DOCUMENTS

EP           2683225 A1     1/2014
JP        H05-196955 A      8/1993
(Continued)

OTHER PUBLICATIONS

International Search Report dated Jul. 7, 2015 issued in PCT/JP2015/063307.

*Primary Examiner* — Albert H Cutler
(74) *Attorney, Agent, or Firm* — Scully, Scott, Murphy & Presser, P.C.

(57) ABSTRACT

An image pickup unit includes: an image pickup device on which an image pickup section is formed; a circuit board having a main surface on which a connection terminal electrically connected with the image pickup section is disposed; an intermediate wiring board including a substrate, an adhesive layer and a wiring pattern, in which a first electrode of the wiring pattern is electrically connected with the connection terminal; a cable having a core wire; and a holding substrate configured to hold the core wire with a second electrode and fixed to the intermediate wiring board by the adhesive layer in a state that the core wire and the second electrode are electrically connected by being in close contact.

12 Claims, 9 Drawing Sheets

(51) Int. Cl.
*H05K 1/11* (2006.01)
*H04N 5/225* (2006.01)
*G02B 23/24* (2006.01)
*A61B 1/00* (2006.01)
*H05K 3/32* (2006.01)
*H05K 1/14* (2006.01)

(52) U.S. Cl.
CPC ........... *H04N 5/2253* (2013.01); *H05K 1/117* (2013.01); *H05K 3/32* (2013.01); *H05K 3/361* (2013.01); *H04N 2005/2255* (2013.01); *H05K 1/147* (2013.01); *H05K 2201/10121* (2013.01); *H05K 2201/10446* (2013.01); *H05K 2201/10962* (2013.01); *H05K 2201/2009* (2013.01)

(58) Field of Classification Search
CPC ............. H05K 3/32; H05K 1/147; H05K 2201/10446; H05K 2201/10962; H05K 2201/2009; H05K 2201/10121; H05K 1/117; H05K 3/361
See application file for complete search history.

(56) References Cited

U.S. PATENT DOCUMENTS

| | | | | |
|---|---|---|---|---|
| 2008/0091064 | A1* | 4/2008 | Laser | A61B 1/053 600/109 |
| 2008/0117324 | A1* | 5/2008 | Minamio | H04N 5/2253 348/340 |
| 2010/0201794 | A1* | 8/2010 | Kido | A61B 1/00124 348/65 |
| 2010/0231702 | A1 | 9/2010 | Tsujimura et al. | |
| 2011/0211053 | A1* | 9/2011 | Nakayama | A61B 1/051 348/76 |
| 2012/0206583 | A1* | 8/2012 | Hoshi | A61B 1/042 348/76 |
| 2013/0039065 | A1* | 2/2013 | Okabe | H05K 3/202 362/249.02 |
| 2014/0003018 | A1 | 1/2014 | Fujimori | |
| 2014/0249368 | A1* | 9/2014 | Hu | H04N 5/2253 600/109 |

FOREIGN PATENT DOCUMENTS

| | | | |
|---|---|---|---|
| JP | 11-162539 | * | 6/1999 |
| JP | H11-162539 A | | 6/1999 |
| JP | 2004-014235 A | | 1/2004 |
| JP | 2006-034458 A | | 2/2006 |
| JP | 2009-082504 A | | 4/2009 |
| JP | 2012-183330 A | | 9/2012 |
| JP | 2012-186301 A | | 9/2012 |
| WO | WO 2009/041723 A1 | | 4/2009 |
| WO | WO 2012/120742 A1 | | 9/2012 |

* cited by examiner

IMAGE PICKUP UNIT, WIRING BOARD WITH CABLE, AND MANUFACTURING METHOD OF WIRING BOARD WITH CABLE

CROSS REFERENCE TO RELATED APPLICATION

This application is a continuation application of PCT/JP2015/063307 filed on May 8, 2015 and claims benefit of Japanese Application No. 2014-123679 filed in Japan on Jun. 16, 2014, the entire contents of which are incorporated herein by this reference.

BACKGROUND OF THE INVENTION

1. Field of the Invention

The present invention relates to an image pickup unit in which an image pickup device is electrically connected with cables through a circuit board and an intermediate wiring board, a wiring board with cable in which the circuit board is electrically connected with the cables through the intermediate wiring board, and a manufacturing method of the wiring board with cable.

2. Description of the Related Art

For an electronic endoscope including an image pickup unit at a distal end portion of an insertion portion, diameter reduction of the distal end portion is demanded to reduce invasiveness. In order to reduce a diameter of the distal end portion, a small-sized image pickup unit is needed.

Japanese Patent Application Laid-Open Publication No. 2006-34458 discloses a small-sized image pickup unit in which an image pickup device and a circuit board mounted with electronic components are connected by an inner lead and the inner lead is bent.

Japanese Patent Application Laid-Open Publication No. 2004-14235 discloses a connecting member that electrically connects a conductor and a conductor without heating by fixing the conductors with an adhesive in a close contact state.

SUMMARY OF THE INVENTION

An image pickup unit in an embodiment of the present invention includes: an image pickup device having a light receiving surface on which an image pickup section is formed; a circuit board having a main surface on which a connection terminal electrically connected with the image pickup section is disposed; an intermediate wiring board including a substrate, an adhesive layer and a wiring pattern, in which a first electrode of the wiring pattern having the first electrode and a second electrode is electrically connected with the connection terminal; a cable having a core wire; and a holding substrate configured to hold the core wire with the second electrode and fixed to the intermediate wiring board by the adhesive layer in a state that the core wire and the second electrode are electrically connected by being in close contact.

In addition, a wiring board with cable in another embodiment includes: a cable having a core wire; an intermediate wiring board including a substrate, an adhesive layer, and a wiring pattern having a first electrode and a second electrode; a holding substrate configured to hold the core wire with the second electrode and fixed to the intermediate wiring board by the adhesive layer in a state that the core wire and the second electrode are electrically connected by being in close contact; and a circuit board having a main surface on which a connection terminal electrically connected with the first electrode of the wiring pattern of the intermediate wiring board is disposed.

Further, a manufacturing method of a wiring board with cable in another embodiment includes: a step of preparing an intermediate wiring board including a substrate, an adhesive layer formed of an ultraviolet curing type resin, a wiring pattern having a first electrode and a second electrode, and a sticky layer pattern, a holding substrate made to adhere to the intermediate wiring board, and a cable having a core wire electrically connected with the wiring pattern; a step of holding the core wire of the cable by the holding substrate and the second electrode, and temporarily fixing the intermediate wiring board and the holding substrate through the sticky layer pattern in a state that the core wire and the second electrode are electrically connected by being in close contact; a step of inspecting a connection state of the cable; and a step of curing the adhesive layer by ultraviolet ray irradiation, and adhering and fixing the intermediate wiring board and the holding substrate.

DETAILED DESCRIPTION OF THE PREFERRED EMBODIMENT(S)

First Embodiment

Figure 1:
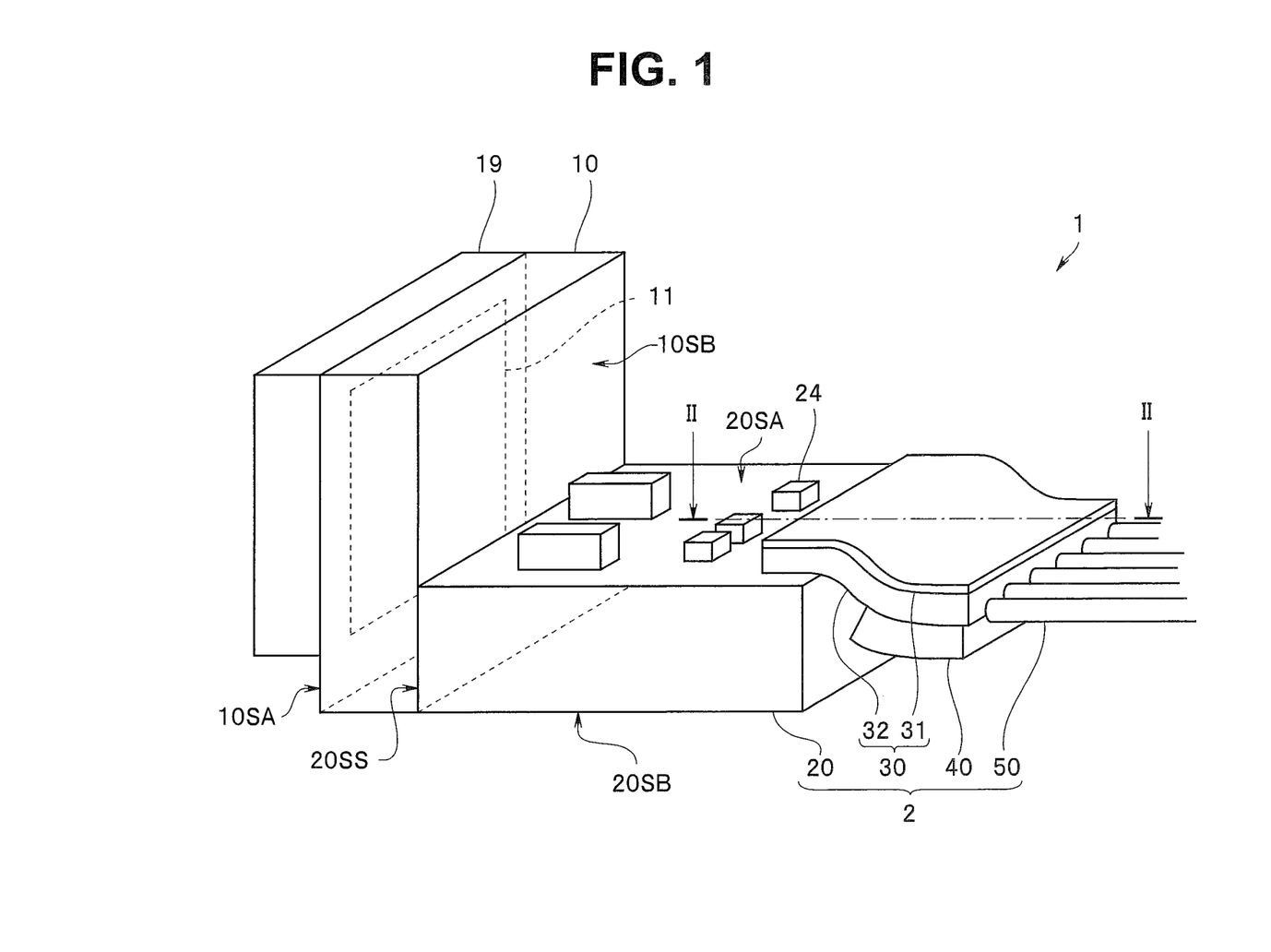
FIG. 1 is a perspective view of an image pickup unit in a first embodiment.
Figure 2:
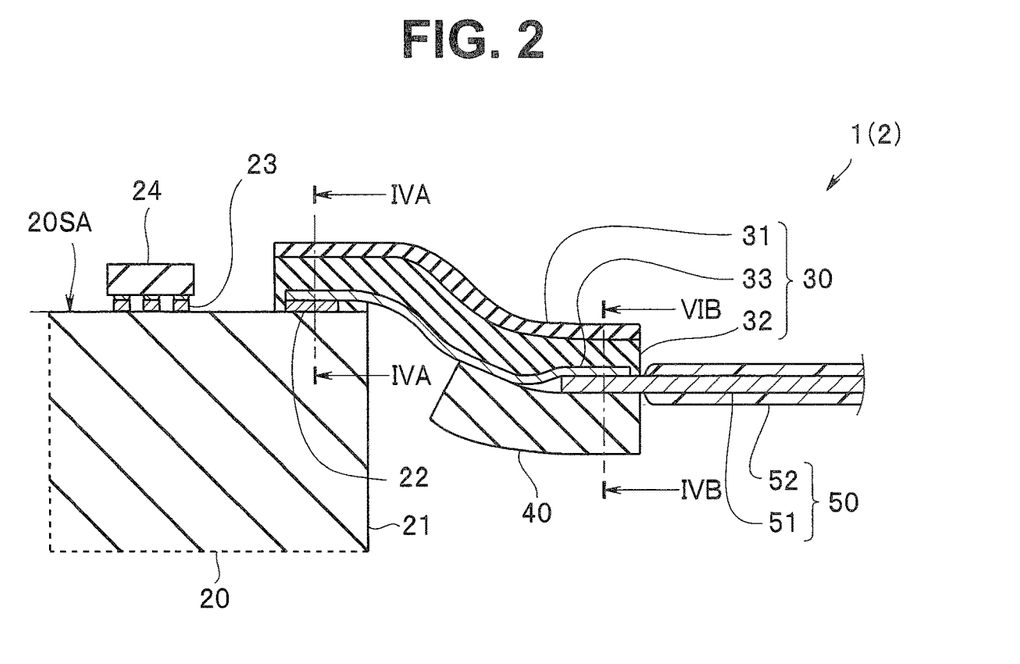
FIG. 2 is a sectional view of a wiring board with cable of the image pickup unit in the first embodiment.

As illustrated in FIG. 1 and FIG. 2, an image pickup unit 1 in the present embodiment includes an image pickup device 10, a glass lid 19, a circuit board 20, an intermediate wiring board 30, a holding substrate 40, and cables 50. Note that the circuit board 20, the intermediate wiring board 30, the holding substrate 40 and the cables 50 configure a wiring board with cable 2 in the embodiment.

Note that, in the following description, the drawings based on the individual embodiments are schematic, it should be noted that a relation between a thickness and a width of individual parts and a ratio of the thicknesses of the respective parts or the like are different from the actual ones, and even between the drawings, a part where the relation of mutual dimensions or the ratio is different is sometimes included.

The image pickup device 10 includes a rectangular parallelepiped semiconductor having a light receiving surface 10SA and a back surface 10SB. On the light receiving surface 10SA of the image pickup device 10, an image pickup section 11 such as a CCD or a CMOS image sensor is formed. The glass lid 19 formed of plate glass is made to adhere to the light receiving surface 10SA of the image pickup device 10 in order to protect the image pickup section 11. Note that the glass lid 19 is not a component essential to the image pickup unit 1.

The circuit board 20 is a wiring board having a plurality of wiring lines (not shown in the figure), a base material of which is ceramic or a glass epoxy resin, for example. The circuit board 20 is a rectangular parallelepiped having a main surface 20SA and a side face 20SS orthogonal to the main surface 20SA.

Though not shown in the figure, a back surface electrode connected with the image pickup section 11 of the image pickup device 10 through a flexible wiring board for example is provided on a back surface 20SB opposing the main surface 20SA, and the back surface electrode is connected with connection terminals 22 and 23 of the main surface 20SA through a through wiring line or an internal wiring line or the like. To the connection terminal 23, electronic components 24 are soldered and mounted.

For the plurality of cables 50 configured to supply electric power and driving signals to the image pickup device 10 and transmit image pickup signals from the image pickup device 10, a core wire 51 is covered with a jacket 52 formed of an insulating resin. For example, an outer diameter of the core wire 51 is equal to or larger than 20 μm and is equal to or smaller than 250 μm, and an outer diameter of the jacket 52 (cable 50) is equal to or larger than 100 μm and is equal to or smaller than 400 μm.

The intermediate wiring board 30 is a flexible wiring board for connecting the cables 50 and the circuit board 20. The intermediate wiring board 30 includes a substrate 31, and an adhesive layer 32 disposed on the substrate 31.

By the adhesive layer 32, one end of the intermediate wiring board 30 is made to adhere to an end portion of the main surface 20SA of the circuit board 20, and the other end is made to adhere to the holding substrate 40. The holding substrate 40 is formed of a flexible resin. Then, the cables 50 are electrically connected with the intermediate wiring board 30 by being held by the intermediate wiring board 30 and the holding substrate 40.

Next, using FIG. 2 to FIG. 4, electrical connections in the image pickup unit 1 (the wiring board with cable 2) will be described further. Note that "electrically connected" is simply referred to as "connected" hereinafter.

As already described, on the main surface 20SA of the circuit board 20, the plurality of connection terminals 23 to which the electronic components 24 are bonded with solder and the plurality of connection terminals 22 for connecting the intermediate wiring board 30 are disposed. The connection terminals 22 and 23 are connected with the image pickup section 11 through a wiring line not shown in the figure.

Figure 3:
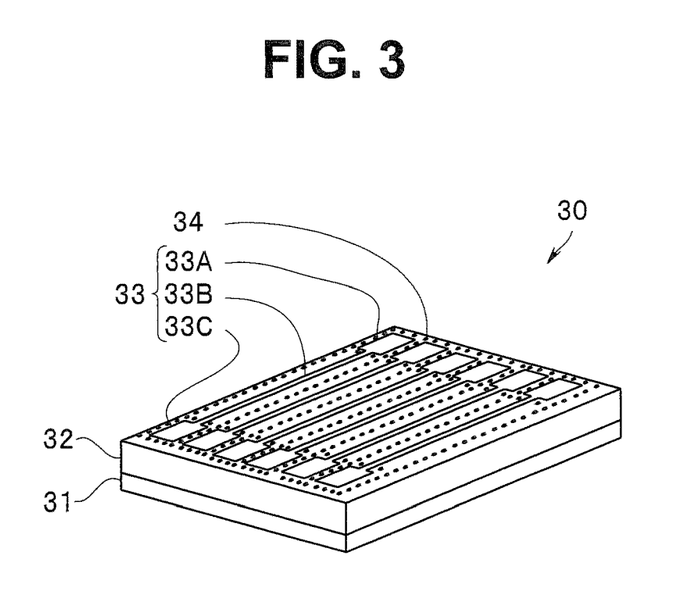
FIG. 3 is a perspective view of an intermediate wiring board of the image pickup unit in the first embodiment.

As illustrated in FIG. 3, the intermediate wiring board 30 includes the flexible substrate 31, the adhesive layer 32 disposed on an entire surface of one surface of the substrate 31, and a plurality of wiring patterns 33 disposed on the adhesive layer 32. The wiring pattern 33 has a wiring section 33B, a first electrode 33C extended from a front end portion of the wiring section 33B, and a second electrode 33A extended from a rear end portion.

In addition, as described later, to the intermediate wiring board 30, a plurality of sticky layer patterns 34 are disposed in order to temporarily fix the circuit board 20.

Note that, hereinafter, "adhere" refers to a state of being "fixed" through an adhesive layer which is cured and turned to a solid. In contrast, "stick" refers to a state of being "temporarily fixed" through a sticky layer which contains a gel component and in which flexibility is maintained. In "temporary fixing", peeling and re-sticking are possible. In addition, "close contact" refers to a contact state in which a contact part is not a point but a line or a surface.

Figure 4A:
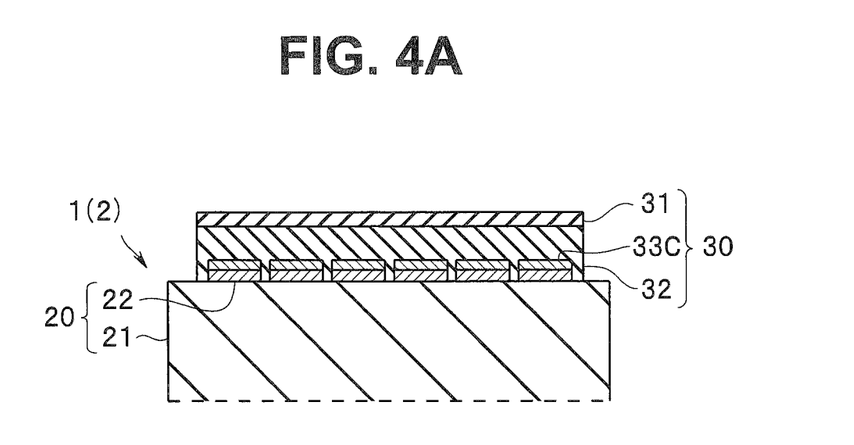
FIG. 4A is a sectional view along an IVA-IVA line in FIG. 2 of the wiring board with cable of the image pickup unit in the first embodiment.

Then, as illustrated in FIG. 4A, the intermediate wiring board 30 is fixed to the circuit board 20 by the adhesive layer 32. The first electrode 33C of the wiring pattern 33 is connected by being in close contact with the connection terminal 22.

Figure 4B:
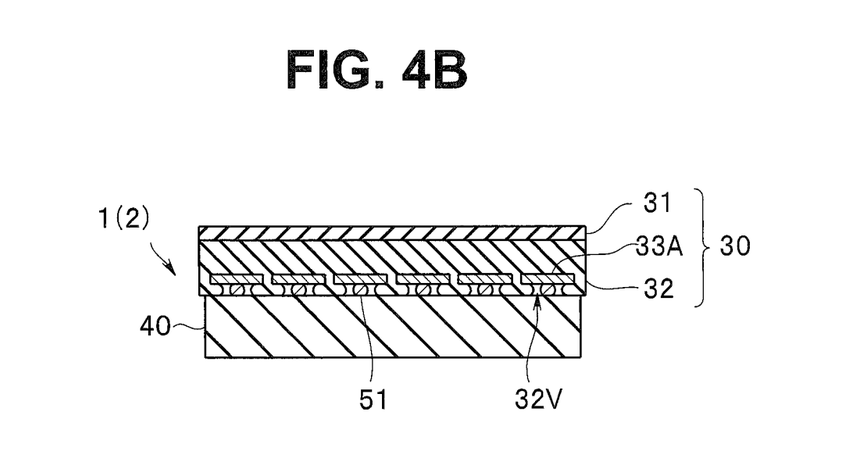
FIG. 4B is a sectional view along an IVB-IVB line in FIG. 2 of the wiring board with cable of the image pickup unit in the first embodiment.

In contrast, as illustrated in FIG. 4B, the second electrode 33A holds the core wire 51 of the cable 50 with the holding substrate 40. Thus, the core wire 51 and the second electrode 33A are connected by being in close contact.

Note that, since the adhesive layer 32 before curing is soft, the adhesive layer 32 expands below the second electrode 33A as well when pressurized by the holding substrate 40. Since a connection part of the core wire 51 and the second electrode 33A is sealed by the adhesive layer 32, connection reliability is high. Note that, while a space 32V into which the adhesive layer 32 does not expand is formed around the core wire 51 in the wiring board with cable 2 illustrated in FIG. 4B, the core wire 51 may be covered with the adhesive layer 32 without the space 32V.

The first electrode 33C is connected with the connection terminal 22 by being in contact with the connection terminal 22 without interposing another member, and the second electrode 33A is also connected with the core wire 51 by being in contact with the core wire 51 without interposing another member.

The adhesive layer 32 of the intermediate wiring board 30 is formed of a thermosetting resin to be cured at or below 250° C., or an ultraviolet curing type resin. Therefore, all the connection parts are connected in a process at a temperature lower than a melting temperature of solder which bonds the electronic components 24, differently from bonding by the solder or the like requiring heating above 250° C.

Therefore, in the image pickup unit 1 and the wiring board with cable 2, the solder of the electronic components 24 mounted on the circuit board 20 does not remelt, and reliability is high. In addition, the image pickup unit 1 has no risk that the image pickup device 10 is damaged by heat, and the reliability is high. In addition, since the connection part of the core wire 51 and the second electrode 33A is not exposed to the outside by being held by the intermediate wiring board 30 and the holding substrate 40, the reliability against an environment such as humidity is high.

In addition, since there is no risk that the solder remelts, the electronic components 24 can be arranged near the second electrode 33A of the circuit board 20. Therefore, the image pickup unit 1 and the wiring board with cable 2 are easily miniaturized.

Note that, before the image pickup device 10 and the electronic components are disposed to the circuit board 20, the intermediate wiring board 30 may be bonded to the circuit board 20 by the solder or the like and only the connection part with the cables 50 may be fixed by the adhesive layer 32.

In addition, since the intermediate wiring board 30 having the sticky layer patterns 34 can be easily stuck again even if misalignment occurs, the image pickup unit 1 (the wiring board with cable 2) is easy to manufacture.

Figure 5:
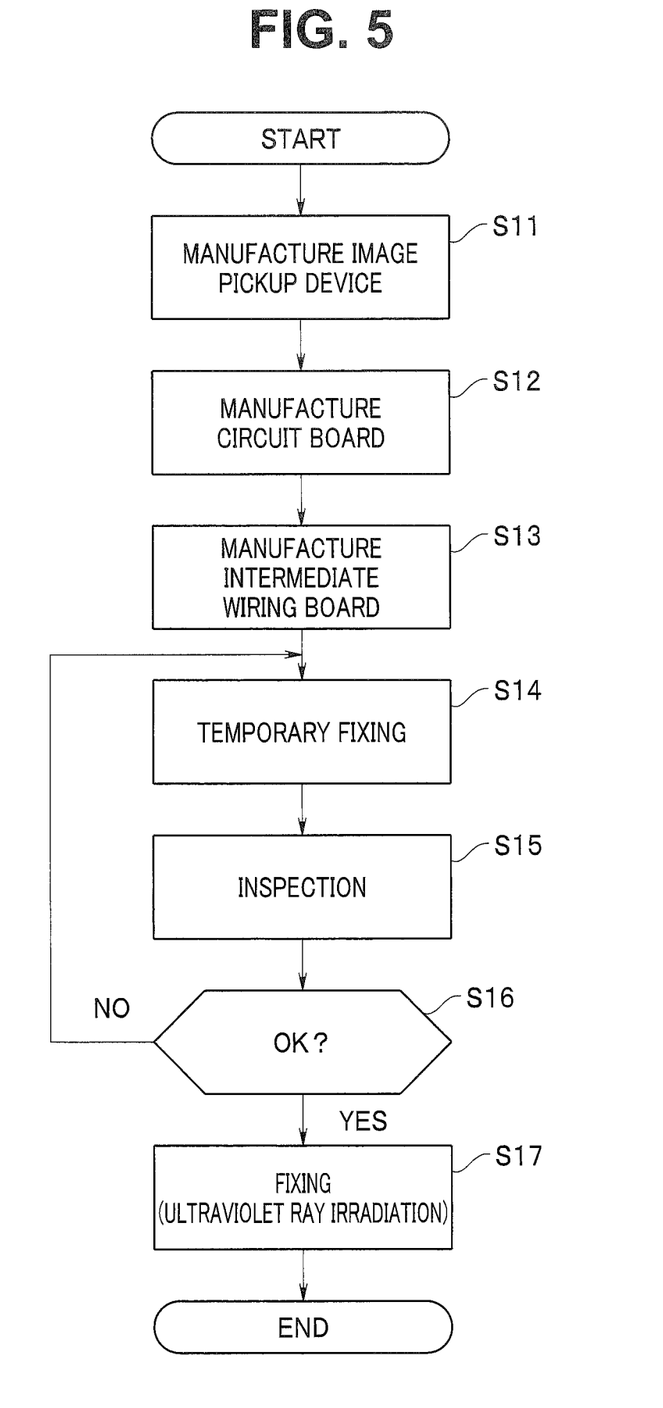
FIG. 5 is a flowchart of a manufacturing method of the image pickup unit in the first embodiment.

Next, along a flowchart in FIG. 5, a manufacturing method of the image pickup unit 1 will be described.

<Step S11> Manufacture Image Pickup Device

Using a well-known semiconductor manufacturing technique, the plurality of image pickup sections 11 are formed on a wafer formed of a semiconductor such as silicon. A microlens array and a color filter or the like may be disposed on the image pickup sections 11. By cutting and separating the silicon wafer, a rectangular parallelepiped image pickup device 10 is manufactured.

Note that the glass lid 19 may be made to adhere to the image pickup device 10 after separation, or may be formed by making a bar-shaped (square pole shape) glass plate adhere in a wafer stage and then performing the separation.

<Step S12> Manufacture Circuit Board

The circuit board 20 is designed and manufactured according to specifications of the image pickup unit 1. For the circuit board 20, the connection terminals 22 and 23 formed of conductors are disposed on the main surface 20SA.

The circuit board 20 may be a multilayer wiring board in which a conductor layer formed of copper or the like to be a wiring line and an insulation layer formed of ceramic or an insulating resin or the like are laminated two or more times, or may be a double-faced wiring board having a through wiring line. In addition, the circuit board 20 may be a component incorporating wiring board in which the electronic components are mounted not only on the main surface 20SA but also in an inside.

To the circuit board 20, the plurality of electronic components 24 are soldered and bonded at a temperature over 250° C. for example. Note that, since the plurality of electronic components 24 are disposed on the narrow main surface 20SA, it is preferable that the electronic components 24 be a BGA (ball grid array) type or a CSP (chip scale package) type in which an interval of balls is shorter than that of the BGA type. The circuit board 20 which is a wiring board mounted with the electronic components 24 has a circuit that primarily processes signals that are transmitted and received.

For the circuit board 20, the side face 20SS is made to adhere to the back surface 10SB of the image pickup device 10 using an adhesive or the like. Further, the circuit board 20 is connected with the image pickup device 10 through a flexible wiring board or the like.

<Step S13> Manufacture Intermediate Wiring Board

As illustrated in FIG. 3, the intermediate wiring board 30 includes the flexible substrate 31, the adhesive layer 32, and the plurality of wiring patterns 33. From viewpoints of flexibility, Young's modulus, and adhesion strength with the adhesive or the like, the substrate 31 is formed of PET (polyethylene terephthalate), PEN (polyethylene naphthalate), or PI (polyimide) for example, and it is preferable that a thickness be equal to or larger than 10 μm and equal to or smaller than 250 μm.

The adhesive layer 32 is formed of the ultraviolet curing type resin or the thermosetting resin to be cured at or below 250° C. It is preferable that the thickness of the adhesive layer 32 be equal to or larger than 10 μm and is equal to or smaller than 500 μm. The adhesive layer 32 may be disposed on an entire surface of the substrate 31 or may be partially disposed. Note that, in the case of the intermediate wiring board 30 including the adhesive layer 32 formed of the ultraviolet curing type resin, the substrate 31 is selected from a material which does not cut off ultraviolet rays for curing.

The wiring pattern 33 formed of a copper layer includes the first electrode 33C, the wiring section 33B and the second electrode 33A. Note that the first electrode 33C and the second electrode 33A and the wiring section 33B may have the same width and an end portion of the wiring section 33B may have a function of the first electrode 33C and the second electrode 33A.

The intermediate wiring board 30 has the sticky layer patterns 34 for temporary fixing, further. It is preferable that the thickness of the sticky layer pattern 34 be equal to or larger than 10 μm and is equal to or smaller than 500 μm. For example, the sticky layer pattern 34 is formed of a gelatinous sticker, a gel fraction of which is equal to or larger than 30 wt. % and is equal to or smaller than 70 wt. %. For the gel fraction, the sticker is immersed in toluene, and mass after drying insoluble matters that remain after leaving the sticker for 24 hours is measured and expressed by a percentage to original mass.

Figure 6A:
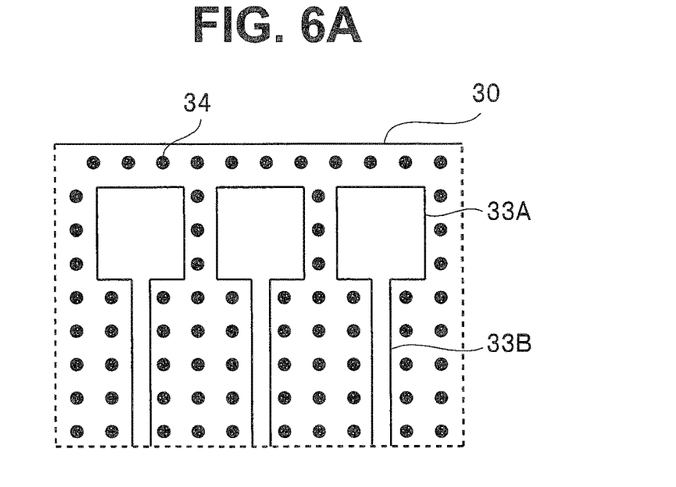
FIG. 6A is a top view of the intermediate wiring board of the image pickup unit in the first embodiment.

As illustrated in FIG. 6A, the sticky layer patterns 34 are disposed as dot patterns on the adhesive layer 32 around the wiring patterns 33. Note that the sticky layer patterns 34 may be arranged not only around the wiring patterns 33 but also on the entire surface of the intermediate wiring board 30.

The intermediate wiring board 30 can be temporarily fixed by the sticky layer patterns 34. That is, peel strength (180-degree peeling test ISO29862 2007) of the intermediate wiring board 30 stuck through the sticky layer patterns 34 is equal to or lower than 0.05 N/10 mm, for example, easy peeling is possible, and re-sticking is also possible. Note that, peel strength of the adhesive layer 32 after curing processing in contrast is equal to or higher than 0.5 N/10 mm, for example.

In addition, for noise reduction for transmission signals, it is preferable that, for the intermediate wiring board 30, a metal film formed of copper or the like be disposed on an almost entire surface opposing the surface where the wiring patterns 33 are disposed.

Figure 6B:
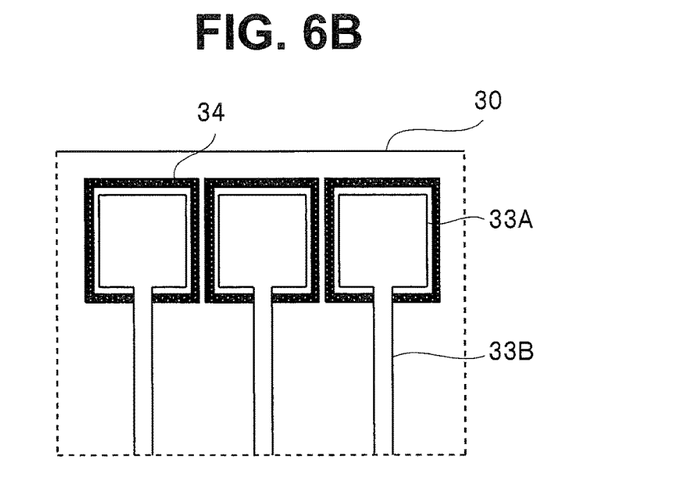
FIG. 6B is a top view of the intermediate wiring board of the image pickup unit in a modification 1 of the first embodiment.
Figure 6C:
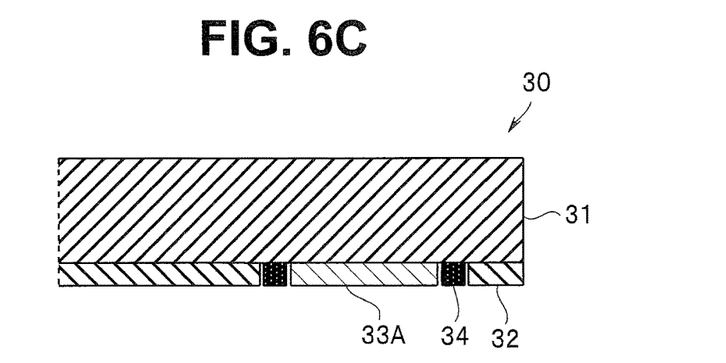
FIG. 6C is a sectional view of the intermediate wiring board of the image pickup unit in a modification 2 of the first embodiment.

Note that, the sticky layer patterns 34 of the intermediate wiring board 30 in a modification 1 illustrated in FIG. 6B are arranged in a frame shape only around the second electrode 33A (first electrode 33C). In addition, in the intermediate wiring board 30 in a modification 2 illustrated in FIG. 6C, the patterned adhesive layer 32, the sticky layer patterns 34 and the wiring patterns 33 are respectively disposed on the substrate 31. That is, the adhesive layer 32 is not required to be disposed on the entire surface of the intermediate wiring board, and the wiring patterns 33 are not required to be disposed on the adhesive layer 32.

Further, though not shown in the figure, in the intermediate wiring board, the adhesive layer may have a function of the sticky layer pattern of the low peel strength before the curing processing. In other words, the sticky layer pattern may function as the adhesive layer of the high peel strength by the curing processing. Further, the substrate 31 of the intermediate wiring board may have a function of the adhesive layer 32.

That is, the intermediate wiring board in various kinds of forms capable of being temporarily fixed and fixed to another member can be used.

For the intermediate wiring board 30, after a conductor film is formed on the entire surface of the adhesive layer 32 for example, by preparing an etching mask by a photolithographic method and etching an unneeded conductive film, the wiring patterns 33 can be accurately manufactured. Since a disposition pitch of the plurality of wiring patterns 33 can be narrowed by the photolithographic method, the image pickup unit 1 has a small size.

In addition, since the intermediate wiring board 30 and the holding substrate 40 are flexible and bent, adjustment can be made according to an arrangement position of the cables 50 or the like, and a length of the image pickup unit 1 can be made almost the same as a length of an image pickup unit not using the intermediate wiring board 30.

Note that, in the case that the length of the intermediate wiring board 30 is short, a non-flexible glass substrate, a ceramic substrate or a resin substrate with high Young's modulus or the like can be used for the substrate 31 of the intermediate wiring board 30 and the holding substrate 40.

<Step S14> Temporary Fixing

The cables 50 to be connected with the intermediate wiring board 30 and the holding substrate 40 to be made to adhere to the intermediate wiring board 30 are manufactured. Note that the holding substrate 40 is formed of the same insulating resin as the substrate 31. Note that the image pickup device or the like may not be newly manufactured and instead the image pickup device or the like of predetermined specifications manufactured outside may be obtained.

The first electrodes 33C of the intermediate wiring board 30 are pressurized to the connection terminals 22 of the circuit board 20 and temporarily fixed by the sticky layer patterns 34 in the state of being connected by being in close contact. Note that, when temporary fixing is performed, the adhesive layer 32 is also brought into close contact with the circuit board 20, however, since curing is not performed yet, influence on the peel strength by the adhesive layer 32 is extremely small and can be ignored.

In addition, the core wires 51 of the cables 50 are held between the second electrodes 33A of the intermediate wiring board 30 and the holding substrate 40, and are temporarily fixed by the sticky layer patterns 34. Note that, since the intermediate wiring board 30 is flexible as far as the end portion, when the intermediate wiring board 30 is pressurized by the core wires 51, the second electrodes 33A are defaulted along an external shape of the core wires 51, brought into close contact, and connected.

The second electrodes 33A and the core wires 51 are just in close contact, and are not bonded by the solder or a conductive member or the like. Note that, in order to increase a contact area, a distal end portion of the core wires 51 in a cylindrical shape may be strongly pressurized before being connected with the second electrodes 33A and a cross section may be plastically deformed into a roughly rectangular shape. In addition, for reduction of contact resistance, it is preferable that a surface of at least any of the second electrodes 33A and core wires 51 be covered with a layer formed of gold or the like which is soft and is not easily oxidized. Further, it is preferable that a metal layer formed of the gold or the like be disposed also on a surface that holds the core wires 51 of the holding substrate 40.

Note that a shield line (ground potential line) not shown in the figure of the cables 50 is also held between the second electrodes 33A to be a ground potential and the holding substrate 40 similarly to the core wires 51.

<Step S15, Step S16> Inspection

A connection state of the temporarily fixed intermediate wiring board 30 is inspected. The inspection may be a visual inspection, or electric power may be supplied through the cables 50 to the image pickup device 10 and an operation may be actually confirmed.

In the case that there is no problem in the connection state (S16: YES), processing of S17 is performed. On the other hand, in the case that there is a problem in the connection state (S16: NO), the temporarily fixed intermediate wiring board 30 is peeled and the processing from S14 is performed again.

Note that, in the case that there is a problem in a member such as the image pickup device 10, the circuit board 20 or the cables 50, the member is exchanged for a new member.

By performing the inspection, not only generation of a connection defect but also a defect of any member can be easily coped with in the manufacturing method of the image pickup unit 1, and it is efficient.

<Step S17> Curing

The curing processing of the adhesive layer 32 is performed, and the intermediate wiring board 30 is fixed. The curing processing is selected according to a material of the adhesive layer 32, and for example, irradiation is performed with active energy rays such as ultraviolet rays that are transmitted through the substrate 31 or heat treatment at or below 250° C. is performed.

According to the manufacturing method of the image pickup unit in the present embodiment, since the cables 50 are connected to the circuit board 20 by processing below a solder melting temperature, at a normal temperature for example, the solder of the mounted electronic components 24 does not remelt. Therefore, according to the manufacturing method of the image pickup unit in the present embodiment, the highly reliable image pickup unit 1 can be manufactured. In addition, in the manufacturing method of the image pickup unit in the present embodiment, since the intermediate wiring board 30 can be easily stuck again, manufacture is easy. Also, even in the case that any member is identified as a defective article during a manufacturing process, a conforming article can be manufactured by exchanging the member only, manufacture efficiency can be improved and a cost can be reduced.

Note that, while the image pickup unit 1 including the image pickup device 10 and the manufacturing method of the image pickup unit are described above, it is clear that similar effects are provided also in the wiring board with cable 2 not including the image pickup device and a manufacturing method of the wiring board with cable.

That is, the wiring board with cable 2 in the embodiment includes: cables each having a core wire; an intermediate wiring board including a substrate, an adhesive layer, and wiring patterns each having a first electrode and a second electrode; a holding substrate configured to hold the core wire with the second electrode and fixed to the intermediate wiring board by the adhesive layer in a state that the core wire and the second electrode are electrically connected by being in close contact; and a circuit board having a main surface on which connection terminals electrically connected with the first electrode of each of the wiring patterns of the intermediate wiring board are disposed.

In addition, the manufacturing method of the wiring board with cable in the embodiment includes: a step of preparing an intermediate wiring board including a substrate, an adhesive layer formed of an ultraviolet curing type resin, wiring patterns each having a first electrode and a second electrode, and sticky layer patterns, a holding substrate made to adhere to the intermediate wiring board, and cables each having a core wire electrically connected with the wiring patterns; a step of holding the core wire of each of the cables by the holding substrate and the second electrode, and temporarily fixing the intermediate wiring board and the holding substrate through the sticky layer patterns in a state that the core wire and the second electrode are electrically connected by being in close contact; a step of inspecting a connection state of the cables; and a step of curing the adhesive layer by ultraviolet ray irradiation, and adhering and fixing the intermediate wiring board and the holding substrate.

Second Embodiment

An image pickup unit 1A, a wiring board with cable 2A, and a manufacturing method of the wiring board with cable 2A (referred to as "image pickup unit and the like", hereinafter) in the second embodiment are similar to the image pickup unit 1 and the like in the first embodiment so that same signs are attached to components of the same functions and description is omitted.

Figure 7:
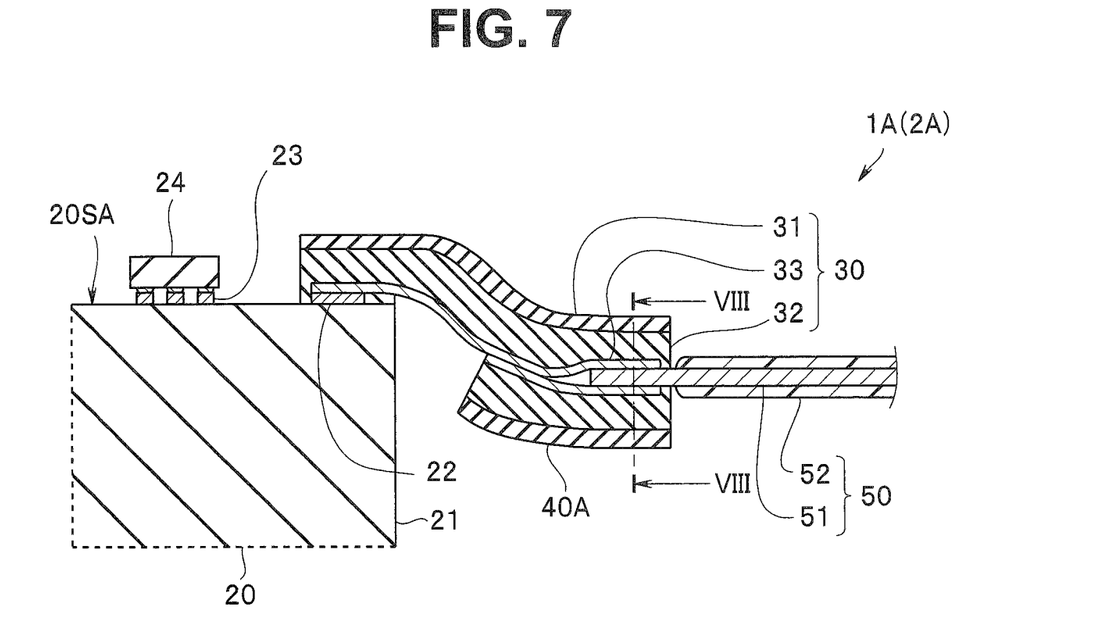
FIG. 7 is a sectional view of the wiring board with cable in a second embodiment.
Figure 8:
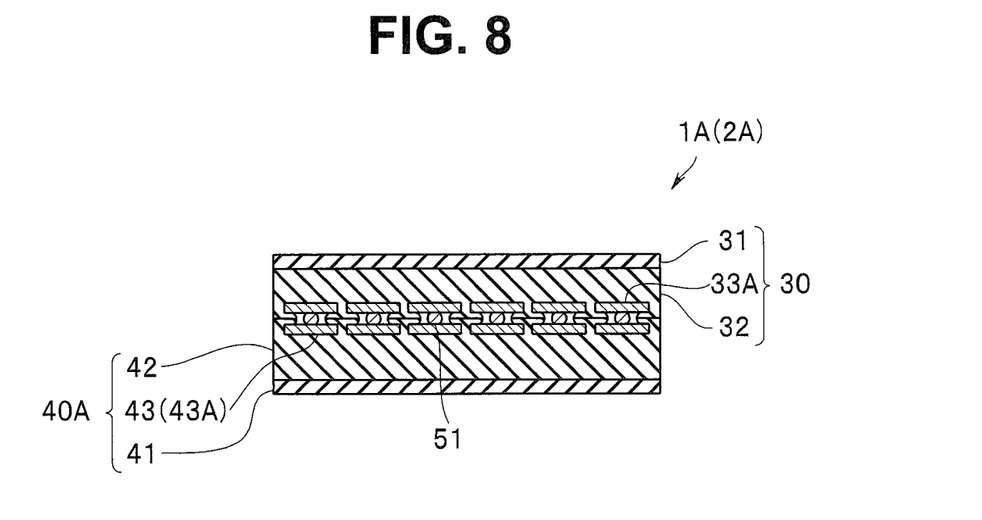
FIG. 8 is a sectional view along VIII-VIII in FIG. 7 of the wiring board with cable in the second embodiment.

As illustrated in FIG. 7 and FIG. 8, in the image pickup unit 1A (the wiring board with cable 2A), the holding substrate 40A has a configuration similar to the intermediate wiring board 30. That is, the holding substrate 40A includes a flexible second substrate 41, a second adhesive layer 42, and a conductor pattern 43 having 2nd-second electrodes 43A (hereinafter referred to as third electrodes 43A). The second substrate 41 has almost the same configuration as the substrate 31, the second adhesive layer 42 has almost the same configuration as the adhesive layer 32, and the third electrodes 43A have almost the same configuration as the second electrodes 33A, respectively. However, as illustrated in FIG. 7, the holding substrate 40A is shorter than the holding substrate 40, and the conductor pattern 43 does not have the first electrodes.

Then, the core wires 51 of the cables 50 are held by the second electrodes 33A and the third electrodes 43A, and the wiring pattern 33 and the conductor pattern 43 are fixed by the adhesive layer 32 and the second adhesive layer 42 in the state of being in close contact and being electrically connected on a side of the circuit board 20 not holding the core wires 51. Note that it is preferable that the holding substrate 40A include the sticky layer patterns for temporary fixing.

The image pickup unit 1A and the like have the effects that the image pickup unit 1 and the like have, and further, since the core wires 51 are held by two conductors (the second electrodes 33A and the second electrodes 43A) from both sides, the connection reliability is higher.

Third Embodiment

An image pickup unit 1B, a wiring board with cable 2B, and a manufacturing method of the wiring board with cable 2B in the third embodiment are similar to the image pickup unit 1 and the like in the first embodiment so that same signs are attached to the components of the same functions and the description is omitted.

Figure 9:
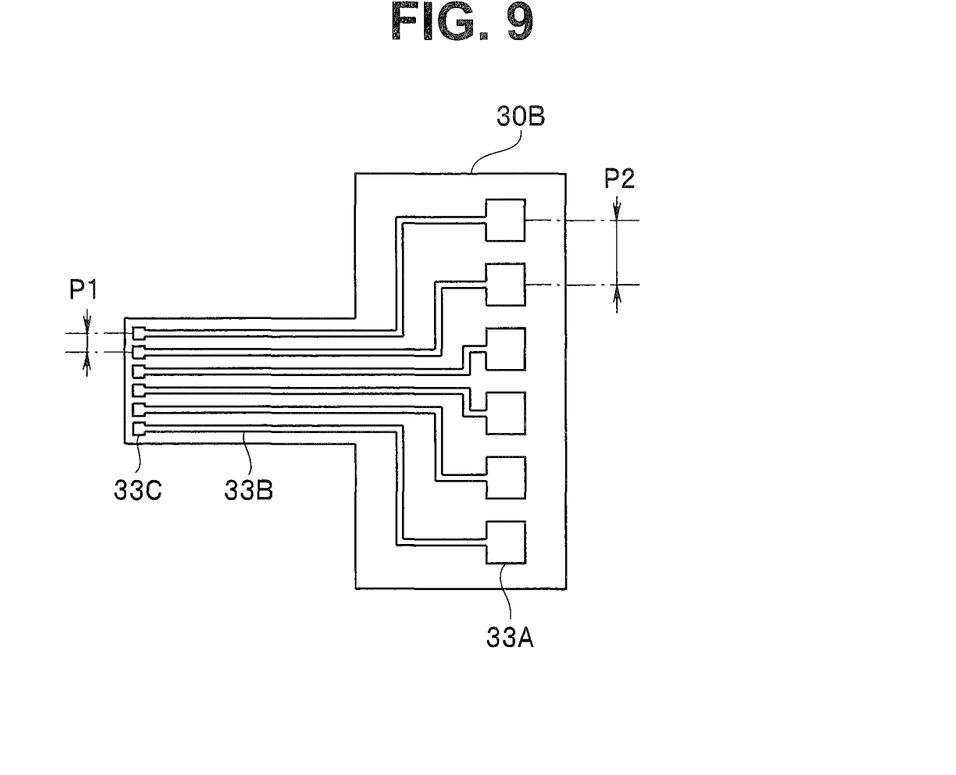
FIG. 9 is a top view of the intermediate wiring board of the image pickup unit in a third embodiment.

As illustrated in FIG. 9, in an intermediate wiring board 30B of the image pickup unit 1B and the like, a disposition pitch P2 of the second electrodes 33A is wider than a disposition pitch P1 of the first electrodes 33C. Therefore, for example, even in the case that the outer diameter of the cables 50 is larger than the disposition pitch P1 of the first electrodes 33C, the core wires 51 can be connected with the second electrodes 33A by the intermediate wiring board 30B.

Figure 10:
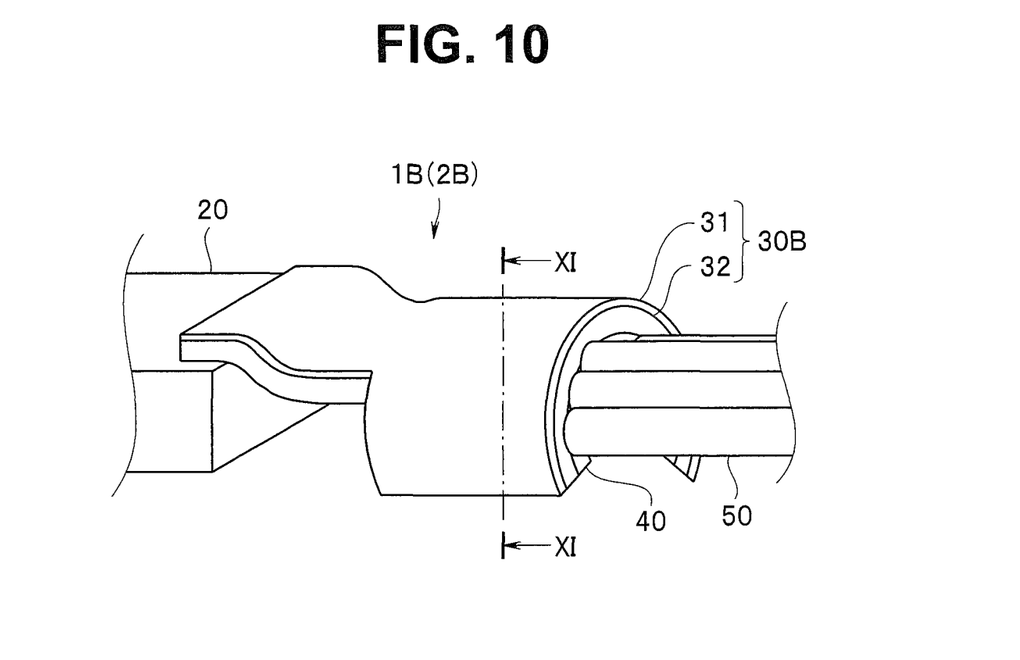
FIG. 10 is a perspective view of the intermediate wiring board of the wiring board with cable in the third embodiment.
Figure 11:
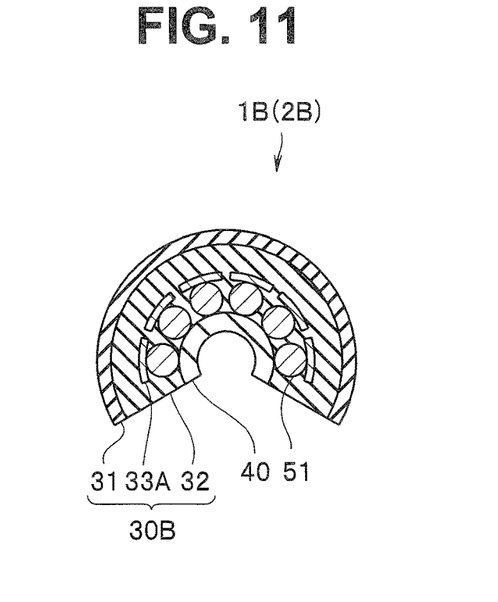
FIG. 11 a sectional view along an XI-XI line in FIG. 10 of the intermediate wiring board of the wiring board with cable in the third embodiment.

Further, as illustrated in FIG. 10 and FIG. 11, in the image pickup unit 1B and the like, it is preferable that the parts holding the core wires 51 of the intermediate wiring board 30B and the holding substrate 40 be bent and deformed in a width direction and turned to a circular arc shape for diameter reduction. That is, since the plurality of cables 50 can be housed inside a space of a small diameter, the diameter of the image pickup unit 1B is small.

Note that, the intermediate wiring board 30B adheres to the holding substrate 40 in FIG. 10 or the like, but may adhere to the holding substrate 40A almost the same as the intermediate wiring board 30B as in the second embodiment.

Fourth Embodiment

An image pickup unit 1C, a wiring board with cable 2C, and a manufacturing method of the wiring board with cable 2C in the fourth embodiment are similar to the image pickup unit 1 and the like in the first embodiment so that same signs are attached to the components of the same functions and the description is omitted.

Figure 12:
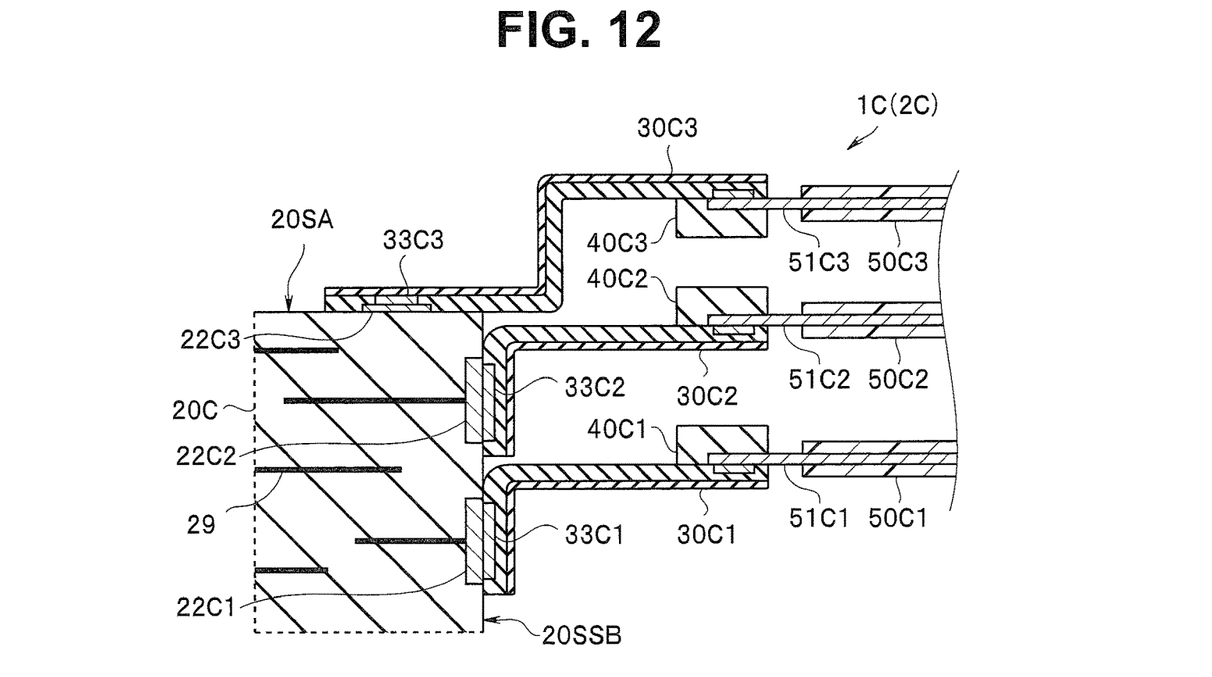
FIG. 12 is a sectional view of the wiring board with cable in a fourth embodiment.

As illustrated in FIG. 12, the circuit board 20C of the image pickup unit 1C is a multilayer wiring board having a plurality of conductor layers 29, and connection terminals 22C1 and 22C2 electrically connected with cables 50C1 and 50C2 that supply the electric power to the image pickup device 10 are disposed on a second side face 20SSB opposing the side face 20SS.

That is, the connection terminal 22C1 disposed on the side face 20SSB is connected with a first electrode 33C1 of an intermediate wiring board 30C1, and a second electrode 33A1 is connected with a core wire 51C1 of the cable 50C1. Similarly, the connection terminal 22C2 disposed on the side face 20SSB is connected with a first electrode 33C2 of an intermediate wiring board 30C2, and a second electrode 33A2 is connected with a core wire 51C2 of the cable 50C2. Then, a connection terminal 22C3 disposed on the main surface 20SA is connected with a first electrode 33C3 of an intermediate wiring board 30C3, and a second electrode 33A3 is connected with a core wire 51C3 of a cable 50C3. Note that the cable 50C1 may be a power supply line, and the cable 50C2 may be the ground potential line. The cable 50C3 transmits image pickup signals from the image pickup device 10.

The image pickup unit 1C (the wiring board with cable 2C) has the effects of the image pickup unit 1 and the like, and since the cables 50C1 and 50C2 that supply the electric power and the cable 50C3 that transmits the image pickup signals are separately arranged further, the image pickup signals are not easily affected by noise due to power transmission. In addition, in order to obtain the effect of a high degree of freedom in arrangement design of the cables and easy miniaturization, an image pickup signal transmission cable may be connected to the side face 20SSB or the cables may be connected only to the side face 20SSB.

Note that the image pickup units 1, 1A and 1B may also have the plurality of intermediate wiring boards similarly to the image pickup unit 1C, and the cable that supplies the electric power may be connected with the connection terminal disposed on the side face 20SSB.

Fifth Embodiment

Figure 13:
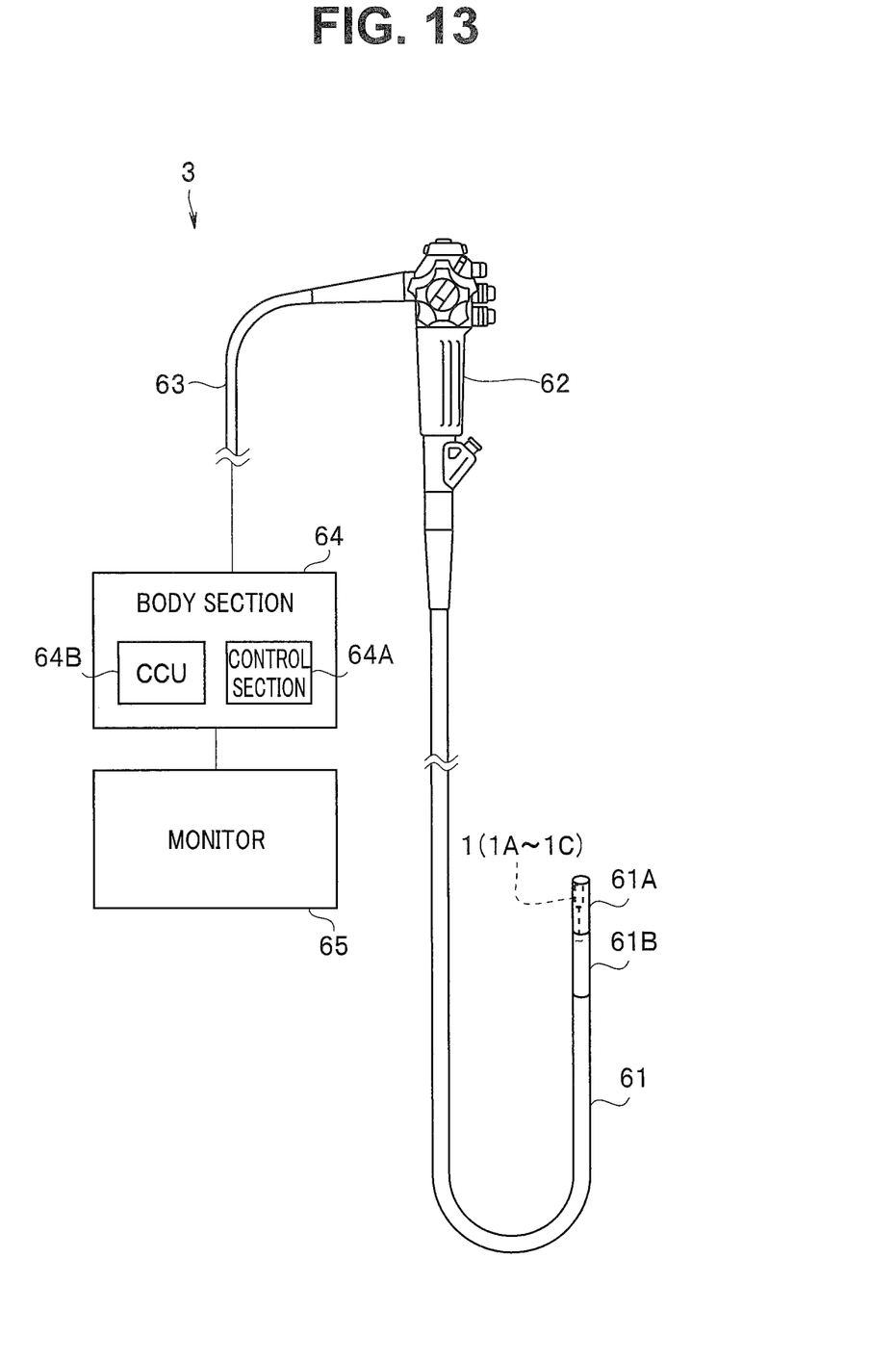
FIG. 13 is a schematic diagram of an endoscope including the image pickup unit in the embodiment.

As illustrated in FIG. 13, an endoscope 3 includes an insertion section 61 to be inserted into a body of a subject, an operation section 62 to be held by an operator, and a universal cord 63 extended from the operation section 62. The universal cord 63 is connected with a body section 64 including a control section 64A and a camera control unit (CCU) 64B or the like, and a monitor 65 is connected to the body section 64. A proximal end portion side of a distal end portion 61A of the insertion section 61 is a bending portion 61B that changes a long axis direction (Z direction) of the distal end portion 61A according to an operation of the operation section 62.

The endoscope 3 is an electronic endoscope in which the already described image pickup units 1 and 1A-1C in the embodiments are disposed at the distal end portion 61A. Since the small-sized and highly reliable image pickup units 1 and 1A-1C are disposed, the endoscope 3 is lowly invasive and is highly reliable.

The present invention is not limited to the above-described embodiments or the like and can be variously changed and modified or the like without changing a gist of the present invention.

What is claimed is:

1. An image pickup unit comprising:
   an image pickup device having a light receiving surface on which an image sensor is formed;
   a circuit board having a main surface on which a connection terminal electrically connected with the image sensor is disposed;
   an intermediate wiring board including a substrate, an adhesive layer and a wiring pattern, in which a first electrode of the wiring pattern having the first electrode and a second electrode is electrically connected with the connection terminal;
   a cable having a core wire; and
   a holding substrate configured to hold the core wire with the second electrode and fixed to the intermediate wiring board by the adhesive layer in a state that the core wire and the second electrode are electrically connected by being in close contact;
   wherein the intermediate wiring board and the circuit board are fixed by the adhesive layer in a state that the connection terminal and the first electrode are electrically connected by being in close contact.

2. The image pickup unit according to claim 1, wherein a sticky layer pattern that temporarily fixes the holding substrate is disposed on the intermediate wiring board.

3. The image pickup unit according to claim 2, wherein, by the sticky layer pattern of the intermediate wiring board, the intermediate wiring board and the circuit board are temporarily fixed in the state of being electrically connected by being in close contact.

4. The image pickup unit according to claim 1, wherein the adhesive layer is formed of an ultraviolet curing type resin.

5. The image pickup unit according to claim 1, wherein the holding substrate includes a second substrate, a second adhesive layer, and a conductor pattern having a third electrode, the core wire is held by the second electrode and the third electrode, and
the wiring pattern and the conductor pattern are fixed by the adhesive layer and the second adhesive layer in the state of being electrically connected by being in close contact at a part of not holding the core wire.

6. The image pickup unit according to claim 1, wherein the circuit board is a multilayer wiring board, and the connection terminal is disposed also on a side face orthogonal to the main surface.

7. The image pickup unit according to claim 1, wherein an electronic component of a BGA type or a CSP type is soldered and mounted on the circuit board.

8. The image pickup unit according to claim 1, wherein a disposition pitch of the second electrode is wider than a disposition pitch of the first electrode.

9. The image pickup unit according to claim 8, wherein parts holding the core wire of the intermediate wiring board and the holding substrate are bent and deformed in a width direction.

10. The image pickup unit according to claim 1, the image pickup unit being disposed at a distal end portion of an endoscope.

11. A wiring board with cable, comprising:
    a cable having a core wire;
    an intermediate wiring board including a substrate, an adhesive layer, and a wiring pattern having a first electrode and a second electrode;
    a holding substrate configured to hold the core wire with the second electrode and fixed to the intermediate wiring board by the adhesive layer in a state that the core wire and the second electrode are electrically connected by being in close contact; and
    a circuit board having a main surface on which a connection terminal electrically connected with the first electrode of the wiring pattern of the intermediate wiring board is disposed;
    wherein the intermediate wiring board and the circuit board are fixed by the adhesive layer in a state that the connection terminal and the first electrode are electrically connected by being in close contact.

12. An image pickup unit comprising:
    an image pickup device having a light receiving surface on which an image sensor is formed;
    a circuit board having a main surface on which a connection terminal electrically connected with the image sensor is disposed;
    an intermediate wiring board including a substrate, an adhesive layer and a wiring pattern, in which a first electrode of the wiring pattern having the first electrode and a second electrode is electrically connected with the connection terminal;
    a cable having a core wire; and
    a holding substrate configured to hold the core wire with the second electrode and fixed to the intermediate wiring board by the adhesive layer in a state that the core wire and the second electrode are electrically connected by being in close contact;
    wherein a sticky layer pattern that temporarily fixes the holding substrate is disposed on the intermediate wiring board.

* * * * *